US011490848B2

(12) United States Patent
Cantillon

(10) Patent No.: US 11,490,848 B2
(45) Date of Patent: Nov. 8, 2022

(54) ADVANCED CARDIAC WAVEFORM ANALYTICS

(71) Applicant: THE CLEVELAND CLINIC FOUNDATION, Cleveland, OH (US)

(72) Inventor: Daniel J. Cantillon, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 241 days.

(21) Appl. No.: 16/878,693

(22) Filed: May 20, 2020

(65) Prior Publication Data

US 2020/0275854 A1 Sep. 3, 2020

Related U.S. Application Data

(63) Continuation-in-part of application No. PCT/US2019/047171, filed on Aug. 20, 2019.
(Continued)

(51) Int. Cl.
*A61B 5/36* (2021.01)
*A61B 5/316* (2021.01)
(Continued)

(52) U.S. Cl.
CPC ............ *A61B 5/316* (2021.01); *A61B 5/0006* (2013.01); *A61B 5/0022* (2013.01); *A61B 5/256* (2021.01);
(Continued)

(58) Field of Classification Search
None
See application file for complete search history.

(56) References Cited

U.S. PATENT DOCUMENTS 5,456,261 A * 10/1995 Luczyk .................. A61B 5/364 600/509
7,671,733 B2 3/2010 McNeal et al.
(Continued)

FOREIGN PATENT DOCUMENTS

CN 107408144 A 11/2017
EP 3079571 A1 10/2016
(Continued)

OTHER PUBLICATIONS

Shen T., Sudden Cardiac Death Detection Methods Based on ECG Biometric Technologies, Shen et al., J Comput Eng Inf Technol 2016, S1 http://dx.doi.org/10.4172/2324-9307.S1-002.
(Continued)

*Primary Examiner* — Kennedy Schaetzle
(74) *Attorney, Agent, or Firm* — Tarolli, Sundheim, Covell & Tummino LLP

(57) ABSTRACT

Systems and methods for electrocardiographic waveform analysis, data presentation and actionable alert generation are described. Electrocardiographic waveform data can be received from a wearable device associated with a patient. A mathematical analysis of at least a portion of the electrocardiographic waveform data can be performed to provide cardiac analytics. In instances where (1) a pathologically prolonged QT interval and (2) an R on T premature ventricular contraction and/or a ventricular tachycardia are detected from the cardiac analytics of the at least a portion of the electrocardiographic waveform data, an actionable alert can be generated and displayed with a visualization of the cardiac analytics.

18 Claims, 8 Drawing Sheets

62 DETERMINE WHETHER QTc IS ABNORMAL FOR A MAJORITY OF SEQUENTIAL HEART BEATS

63 TRIGGER LISTENING WINDOW IF QTc IS ABNORMAL

64 MONITOR ECG FOR ADDITIONAL HIGH RISK FEATURES

65 DETECT HIGH RISK FEATURES

68 DETECT NO HIGH RISK FEATURES

66 PROCESS HIGH RISK FEATURES

69 CLOSE LISTENING WINDOW

67 GENERATE AN ACTIONABLE ALERT

70 NOT GENERATE AN ACTIONABLE ALERT

Related U.S. Application Data

(60) Provisional application No. 62/720,469, filed on Aug. 21, 2018.

(51) Int. Cl.

| | |
|---|---|
| ***A61B 5/00*** | (2006.01) |
| ***A61B 5/363*** | (2021.01) |
| ***A61B 5/364*** | (2021.01) |
| ***G16H 50/20*** | (2018.01) |
| ***A61B 5/35*** | (2021.01) |
| ***A61B 5/256*** | (2021.01) |
| ***A61B 5/366*** | (2021.01) |
| ***A61B 5/353*** | (2021.01) |

(52) U.S. Cl.
CPC ................ *A61B 5/35* (2021.01); *A61B 5/353* (2021.01); *A61B 5/36* (2021.01); *A61B 5/363* (2021.01); *A61B 5/364* (2021.01); *A61B 5/366* (2021.01); *A61B 5/6801* (2013.01); *A61B 5/742* (2013.01); *A61B 5/743* (2013.01); *A61B 5/7405* (2013.01); *A61B 5/746* (2013.01); *A61B 5/747* (2013.01); *A61B 5/7455* (2013.01); *G16H 50/20* (2018.01); *A61B 2560/02* (2013.01)

(56) References Cited

U.S. PATENT DOCUMENTS

| | | | | |
|---|---|---|---|---|
| 8,998,830 | B2 | 4/2015 | Halperin et al. | |
| 9,161,705 | B2 | 10/2015 | Tamil et al. | |
| 2003/0117296 | A1 | 6/2003 | Seely | |
| 2003/0120164 | A1* | 6/2003 | Nielsen ................ | A61B 5/0535 600/513 |
| 2004/0122787 | A1 | 6/2004 | Avinash et al. | |
| 2008/0162182 | A1 | 7/2008 | Cazares et al. | |
| 2009/0171695 | A1 | 7/2009 | Cobbinah et al. | |
| 2010/0131434 | A1 | 5/2010 | Magent et al. | |
| 2010/0268037 | A1 | 10/2010 | Sairamesh | |
| 2011/0066260 | A1 | 3/2011 | Condurso et al. | |
| 2011/0077970 | A1 | 3/2011 | Mellin et al. | |
| 2013/0047113 | A1 | 2/2013 | Hume et al. | |
| 2013/0197942 | A1 | 8/2013 | Chiu et al. | |
| 2013/0231947 | A1 | 9/2013 | Shusterman | |
| 2015/0164349 | A1 | 6/2015 | Gopalakrishnan | |
| 2015/0164438 | A1 | 6/2015 | Halperin et al. | |
| 2015/0221198 | A1 | 8/2015 | Collins, Jr. et al. | |
| 2015/0265164 | A1 | 9/2015 | Gopalakrishnan | |
| 2015/0332012 | A1 | 11/2015 | Edelson et al. | |
| 2016/0113541 | A1* | 4/2016 | Hadley ................ | A61B 5/7203 600/517 |
| 2016/0135706 | A1 | 5/2016 | Sullivan | |
| 2016/0239619 | A1 | 8/2016 | Abou-Hawili et al. | |
| 2016/0278659 | A1 | 9/2016 | Kaib | |
| 2017/0098037 | A1 | 4/2017 | Agassi et al. | |
| 2017/0124279 | A1 | 5/2017 | Rothman | |
| 2017/0238814 | A1 | 8/2017 | Gopalakrishnan | |
| 2018/0272147 | A1* | 9/2018 | Freeman ................ | G16H 50/30 |
| 2018/0325410 | A1 | 11/2018 | Kaib et al. | |
| 2019/0038149 | A1 | 7/2019 | Gopalakrishnan | |
| 2019/0216350 | A1 | 7/2019 | Sullivan et al. | |
| 2019/0298214 | A1 | 10/2019 | Kaib et al. | |

FOREIGN PATENT DOCUMENTS

| | | | |
|---|---|---|---|
| EP | 3204881 | A1 | 8/2017 |
| JP | 2018503885 | A | 8/2018 |
| WO | 2008/087470 | | 7/2008 |
| WO | 2010/024088 | A1 | 3/2010 |
| WO | 20100054088 | A1 | 5/2010 |
| WO | 2015/002945 | A2 | 1/2015 |
| WO | 2015002945 | A2 | 1/2015 |
| WO | 20150089484 | A1 | 6/2015 |
| WO | 2016077786 | A1 | 5/2016 |
| WO | 2016160549 | A1 | 6/2016 |

OTHER PUBLICATIONS

PCT Search Report and Written Opinion for corresponding Application Serial No. PCT/US2019/047141, dated Nov. 4, 2019, pp. 1-11.

Australian Examination Report for corresponding Australian Application Serial No. 2017221258, dated Jun. 3, 2020.

Australian Examination Report for corresponding Australian Application Serial No. 2017221258, dated Mar. 31, 2020, pp. 1-5.

PCT International Search Report corresponding to International Application Serial No. PCT/US2017/017776 dated May 12, 2017.

Sendelbach, Sue, and Marjorie Funk. "Alarm fatigue: a patient safety concern." AACN advanced critical care 24.4 (2013): 378-386.

Schull, Michael J., and Donald A. Redelmeier. "Continuous electrocardiographic monitoring and cardiac arrest outcomes in 8,932 telemetry ward patients." Academic Emergency Medicine 7.6 (2000): 647-652.

Drew, Barbara J., et al. "AHA Scientific Statement: Practice Standards for Electrocardiographic Monitoring in Hospital SettingsAn American Heart Association Scientific Statement From the Councils on Cardiovascular Nursing, Clinical Cardiology, and Cardiovascular Disease in the YoungEndorsed by the International Society of Computerized Electrocardiology and the American Association of Critical-Care Nurses." Journal of Cardiovascular Nursing 20.2 (2005): 76-106.

Australian Examination Report for corresponding Australian Application Serial No. 2017221258, dated Jun. 3, 2019.

Shen, T., et al. "Sudden cardiac death detection methods based on ECG biometric technologies" J Comput Eng Inf Technol 1 (2016).

PCT International Search Report and Written Opinion for corresponding International Application Serial No. PCT/US2019/047151, dated Nov. 4, 2019, pp. 1-11.

* cited by examiner

ADVANCED CARDIAC WAVEFORM ANALYTICS

RELATED APPLICATIONS

This application is a Continuation in Part of International Patent Application Serial No. PCT/US2019/047171, filed on Aug. 20, 2019, which claims the benefit of U.S. Provisional Application No. 62/720,469, entitled "ADVANCED CARDIAC WAVEFORM ANALYTICS," filed Aug. 21, 2018. The entirety of this application is hereby incorporated by reference for all purposes.

TECHNICAL FIELD

The present disclosure relates generally to advanced cardiac waveform analytics (ACWA) and, more specifically, to systems and methods for electrocardiographic waveform analysis, data presentation and actionable alert generation.

BACKGROUND

Electrocardiography is a process of recording electrocardiographic waveforms from a patient's heart. The first known recording of electrocardiographic waveforms was obtained from the human body surface using galvanizing skin electrodes in the early 20$^{th}$ century. Since this first known recording, scientific advances have increased the diagnostic value of electrocardiographic waveforms for cardiovascular disorders. However, contemporary diagnostic tools using electrocardiographic waveforms provide only limited analytic capabilities that do not incorporate important changes in cardiac repolarization, and do not effectively account for confounding physiologic variables including sex, time of day, the presence of baseline abnormalities and individual heart rate variance—thereby limiting contextual interpretation for a given patient. In addition, contemporary tools provide very limited output displays and lack a dynamic tool for the purposes of exchanging, highlighting, annotating and editing key data elements according to clinical relevance for concise export into the electronic medical record.

To complicate matters, over 90% of telemetry alarms neither elicit nor merit clinical responses from bedside health care providers, while up to 44% of cardiopulmonary arrests (CPAs) are not detected appropriately. Only approximately 1 in 4 patients survive an in-hospital CPA according to survival statistics from the American Heart Association. However, advances in non-invasive cardiovascular risk stratification modalities have emerged, including ECG-based methods for real-time detection of cardiac arrhythmias for patients undergoing continuous cardiac rhythm monitoring (CCRM). Unfortunately, no cohesive methodology exists for the collection, processing, analytics, and mobile distribution of the CCRM data to provide advanced warning of sustained atrial or ventricular tachyarrhythmias, cardiopulmonary arrest, critical metabolic derangements or impending heart failure deterioration.

SUMMARY

The present disclosure relates generally to advanced cardiac waveform analytics (ACWA), a method for the collection, processing, analysis, and mobile management of cardiac waveform data (e.g., recorded by a wearable device associated with a patient) by applying advanced risk stratification tools for advance warning of cardiac arrhythmias, including cardiopulmonary arrest, heart failure, decompensation, and critical metabolic derangements. Notably, ACWA can account for not only electrocardiographic waveform data, but also can account for physiologic confounding variables. More specifically, the present disclosure relates to systems and methods for electrocardiographic waveform analysis, data presentation, and actionable alert generation. As an example, the actionable alert can be generated when the electrocardiographic waveform analysis reveals (1) a pathologically prolonged QT interval and (2) an R on T premature ventricular contraction and/or a ventricular tachycardia within the electrocardiographic waveform data.

In one aspect, the present disclosure includes a method for electrocardiographic waveform analysis, data presentation, and actionable alert generation. The method can be performed by a system comprising a processor. The method can include receiving electrocardiographic waveform data from a wearable device associated with a patient; performing a mathematical analysis of at least a portion of the electrocardiographic waveform data to provide cardiac analytics; detecting, from the cardiac analytics of the at least a portion of the electrocardiographic waveform data, a pathologically prolonged QT interval, an R on T premature ventricular contraction, and/or a ventricular tachycardia; and generating an actionable alert when (1) the pathologically prolonged QT interval and (2) the R on T premature ventricular contraction and/or the ventricular tachycardia are detected. When the actionable alert is generated, the actionable alert is displayed with a visualization of the cardiac analytics.

In another aspect, the present disclosure includes a system that can perform electrocardiographic waveform analysis, data presentation, and actionable alert generation. The system includes a non-transitory memory configured to store instructions and a processor to execute the instructions to receive electrocardiographic waveform data from a wearable device associated with a patient, perform a mathematical analysis of at least a portion of the electrocardiographic waveform data to provide cardiac analytics, detect (1) a pathologically prolonged QT interval and (2) an R on T premature ventricular contraction and/or a ventricular tachycardia from the cardiac analytics of the at least a portion of the electrocardiographic waveform data, and generate an actionable alert when the pathologically prolonged QT interval with the R on T premature ventricular contraction and/or the ventricular tachycardia are detected. When the actionable alert is generated, the actionable alert is displayed with a visualization of the cardiac analytics. The system also includes a wireless transceiver to transmit the actionable alert and/or the visualization of the cardiac analytics to one or more medical professionals.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
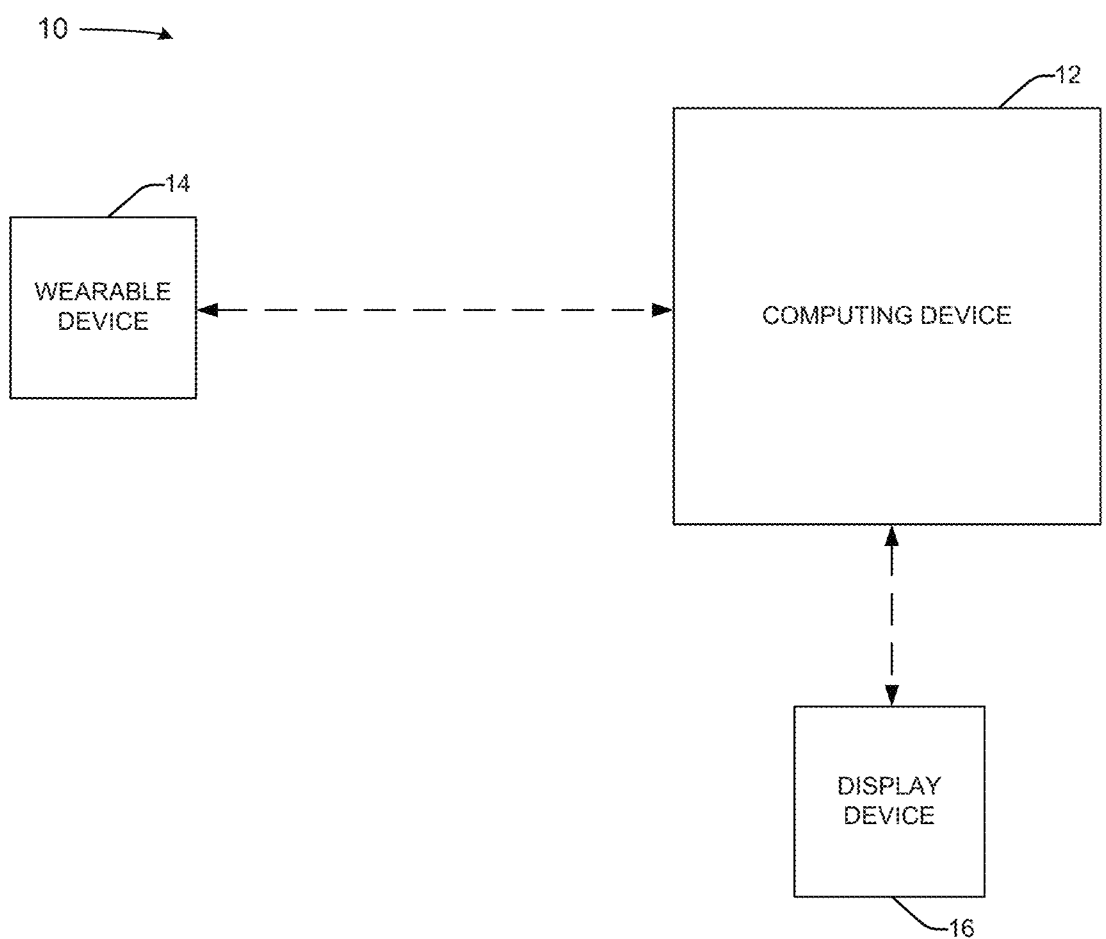
FIG. 1 is a block diagram showing an example of a system that can perform advanced cardiac waveform analytics (ACWA) in accordance with an aspect of the present disclosure.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the term "Advanced Cardiac Waveform Analytics (ACWA)" can refer to an analysis tool, or the use of an analysis tool, for electrocardiographic waveform analysis, data presentation, and actionable alert generation. The analysis tool of ACWA can be specific to an individual patient. ACWA can also refer to the method for the collection, processing, analysis, and mobile management of cardiac waveform data applying advanced risk stratification tools for advance warning of cardiac arrhythmias.

As used herein, the term "electrocardiography (ECG or EKG)" can refer to the process of recording the electrical activity of a patient's heart over a period of time using single or multiple electrodes placed on the patient's skin. The electrodes detect low amplitude electrical changes on the skin that arise from the heart muscle's electrophysiologic pattern of depolarizing and repolarizing during each heartbeat.

As used herein, the term "electrocardiographic (ECG or EKG) waveform" can refer to the plotted tracing of recorded electrical signals from the single or multiple surface skin electrodes (Y-axis) per unit time (X-axis). The electrocardiographic waveform can be collected by a wearable device associated with a patient.

As used herein, the term "electrocardiographic (ECG or EKG) waveform data" can refer to values encapsulated within the electrocardiographic waveform.

As used herein, the term "wearable device" can refer to a technology that can collect electrocardiographic waveforms that is worn on or near a patient's body.

As used herein, the term "cardiac cycle" can refer to the physical contraction and relaxation of the heart's chambers during systole and diastole, along with the accompanying changes in blood flow and blood pressure within the heart and in the blood vessels leading to and from the heart. The cardiac cycle can also refer to the electrocardiographic waveform data elements associated with the electrical depolarization and repolarization of the heart during systole and diastole (e.g., a heartbeat). For each single heartbeat, the electrocardiographic waveform can show P, Q, R, S, and T portions. The QRS portions together can make up the QRS complex. The cardiac cycle can include data elements associated with the human cardiac atria (PR interval) and the human cardiac ventricles (QRS interval, QT interval, RT interval).

As used herein, the term "physiological confounding variable" can refer to an extraneous variable whose presence affects the variables being studied so that the results do not reflect the actual relationship between the variables. Examples of physiological confounding variables include sex, time of day, the presence of baseline abnormalities, specific medication exposures, individual heart rate variance, and the like.

As used herein, the term "cardiac analysis" can refer to direct measurement of electrocardiographic waveform data over the cardiac cycle and mathematical analysis of the electrocardiographic waveform data to provide cardiac analytics. In some instances, the cardiac analysis can account for the presence of physiological confounding variables.

As used herein, the term "cardiac analytics" can refer to values achieved by continuous and categorical descriptive reporting of at least a portion of an electrocardiographic waveform and/or any calculated values according to a mathematical analysis of at least a portion of the electrocardiographic waveform. For example, the cardiac analytics can include at least one of an RR interval, an RT interval, a QT interval, and a corrected QT interval (QTc).

As used herein, the term "mathematical analysis" can refer to the application of mathematics to data (e.g., at least a portion of the electrocardiography waveform data, such as for one or more cardiac cycles to provide cardiac analytics). For example, the mathematics applied can include, but is not limited to, linear or logistic regression analysis of the graphical curves, mathematical derivatives (e.g., areas under the curve) involving pre-specified time series data, and comparisons between real-time and stored fiduciary X, Y coordinates from the electrocardiographic cardiac waveform over the cardiac cycle.

As used herein, the term "machine learning" can refer to software code, routines, and/or methods the computing device and/or rules engine is self-modifying to better associate specific data patterns, including trends, among candidate variables of interest with specific outcomes or clinical findings of interest to determine the probability or likelihood for the specific clinical outcome or occurrence when presented with a similar data pattern or trend. For example, a machine learning application will identify the probability or likelihood of a life-threatening cardiac arrhythmia through the recognition of a particular data pattern that had been previously associated with this event during a training phase of the machine learning process by which the code had been modified over time, and through repetition, to associate specific patterns within the ECG waveform with a high probability of serious life-threatening cardiac arrhythmia.

As used herein, the term "dashboard display" can refer to a graphical user interface to display analyzed cardiac data, results of mathematical analysis, real-time and/or stored electrocardiographic waveform data elements and associated values, and the like.

As used herein, the term "actionable alert", also referred to as an "actionable advisory", can refer to a warning related to the patient of an impending clinically relevant event determined based on one or more cardiac analytics. The actionable alert can comprise visual, auditory, and tactile elements alerting the receiver of the impending clinically relevant event, as generated by a computing device. The impending clinically relevant event can include one or more of a variety of clinical events, conditions, and disease states, including, but not limited to, an atrial or ventricular arrhythmia event (e.g., premature ventricular contraction (PVC), ventricular tachycardia (VT), or the like), congestive heart failure status, impending cardiopulmonary arrest, deterioration of heart failure status, acute coronary syndrome, or clinically important electrolyte derangements or metabolic disturbances in the human body. The actionable alert can be inserted into the patient's electronic medical record at a given time stamp, placed within a graphical user interface display for review by the end user, and/or urgently communicated to the end user via an audio, touch, or visible alarm. For example, the alarm can be transmitted as a text message.

As used herein, the term "modified actionable alert" can refer to an actionable alert that has been altered, modified, or otherwise acted upon by a user for re-transmission to another end user for the purposes of highlighting, annotating, or exchanging clinically relevant information. The modified actionable alert can be inserted into the patient's electronic medical record with the actionable alert at its own given time stamp, and re-transmitted to other medical professionals.

As used herein, the term "electronic medical record (EMR)" can refer to a digital version of a patient's medical history, to be viewed, edited, and added to by medical professionals.

As used herein, the term "time stamp" can refer to a digital record of the time of occurrence of a particular event.

As used herein, the term "baseline" can refer to an average value for a certain parameter. The baseline can be patient-specific, population-specific, or the like.

As used herein, the term "clinically relevant event" can refer to any type of adverse and/or disease-related occurrence that is considered serious (exceeding defined values). Clinically relevant events can be different for different patients.

As used herein, the term "rules engine" can refer to a system that uses rules that each have a condition and an action. In operation, the rules engine can run through all the rules, pick the rules for which a condition is true, and then evaluate the corresponding actions.

As used herein, the term "alarm" can refer to a signal alerting a user. The alarm can be tactilely, auditorily, and/or visually perceptible by a user using touch, hearing, and/or sight, respectively.

As used herein, the term "automated" can refer to being operated automatically without (or with limited) human interference.

As used herein, the term "patient" can refer to any warm-blooded organism including, but not limited to, a human being, a pig, a rat, a mouse, a dog, a cat, a goat, a sheep, a horse, a monkey, an ape, a rabbit, a cow, etc. The subject can be waiting for, undergoing, or in need of medical care.

As used herein, the term "medical professional" can refer to a person providing medical care. A medical professional can be a doctor, a nurse, a nurse practitioner, an emergency medical technician, or any other type of trained caregiver.

As used herein, the term "threshold" can refer to any predetermined value defined as the limit for a particular quantifiable phenomenon; any measured value above or below this limit can initiate a signal, alarm, message, or other form of communication to be sent to systems and users capable of response.

II. Overview

The present disclosure relates generally to advanced cardiac waveform analytics (ACWA) and, more specifically, to systems and methods for electrocardiographic waveform analysis, data presentation, and actionable alert generation. The systems and methods can be used to generate actionable alerts for cardiac events, including, but not limited to, cardiac arrhythmias, heart failure, impending cardiopulmonary arrest, acute coronary syndrome, or critical metabolic abnormalities, when indicated by a certain combination of cardiac analytics. A specific example of cardiac analytics that can trigger the generation of an actionable alert is a co-occurrence of (1) a pathologically prolonged QT interval and (2) an R on T Premature Ventricular Contraction (PVC) and/or Ventricular Tachycardia (VT or V-Tach). In these instances, upon detection of one or more potentially suspicious cardiac analytics, a listening window can be opened to determine whether cardiac events, such as a pathologically prolonged QT interval, an R on T PVC, or VT, occur.

Notably, the cardiac analytics are customized for a patient by determining cardiac events compared to the patient's own baseline electrocardiographic waveform and can account for physiologic confounding variables when determining when to issue the actionable alerts. This allows ACWA to account for physiologic confounding variables when determining when to issue the actionable alerts. Additionally, the present disclosure includes a communication tool by which the displayed actionable alert can be highlighted, edited, annotated, exchanged by medical professionals, and exported to an electronic medical record system according to clinical relevancy.

III. Using ECG to Represent the Cardiac Cycle

An electrocardiograph is one of the most common methods used by medical professionals to monitor a patient's heartbeat and assess cardiac function in a professional health care setting. The waveform displayed on the electrocardiograph represents the entire cardiac cycle of a patient and can be used to determine if the patient suffers from any cardiac maladies. In order to understand an electrocardiographic waveform (also referred to as an electrocardiogram, ECG, EKG, or the like), it is important to have a basic understanding of how the heart and the cardiac cycle work.

A patient's heart includes four chambers: two upper chambers (the right and left atria) and two lower chambers (the right and left ventricles). The right atrium and right ventricle hold deoxygenated blood, while the left atrium and left ventricle hold oxygenated blood that has just returned from the lungs. Four important valves allow blood to pass through the chambers of the heart: (1) the tricuspid valve, which connects the right atrium to the right ventricle; (2) the pulmonic valve, which connects the right ventricle to the pulmonary artery (the structure bringing blood to the lungs for oxygenation); (3) the bicuspid or mitral valve, which connects the left atrium to the left ventricle; and (4) the aortic valve, connecting the left ventricle to the aorta, through which oxygenated blood re-enters the circulatory system. The tricuspid and bicuspid valves connecting the atria and ventricles are collectively referred to as the atrioventricular or AV valves. The pulmonic and aortic valves are called the semilunar valves. In order for the heart to pump blood effectively, the four chambers must contract and relax in a coordinated fashion. This synchronized muscular contraction is referred to as the cardiac cycle. An electrocardiogram (EKG or ECG) tracks the electrical activity underlying these contractions.

The Cardiac Cycle

The cardiac cycle includes periods of muscular relaxation (diastole) and contraction (systole). In the diastolic phase (sometimes called "cardiac diastole"), all of the heart's chambers are relaxed and allowed to fill with blood. The right atrium is filled with deoxygenated blood entering the heart through two large blood vessels, the inferior vena cava and superior vena cava. The left atrium fills with blood returning from the lungs through the pulmonary veins. As the AV valves connecting the atria and ventricles open in the heart's relaxed state the left and right atria both "dump" blood into the right and left ventricles. Simultaneously, the semilunar valves, which connect the ventricles to the pulmonic artery and aorta, are closed and prevent blood from leaving the heart.

In atrial systole, both the left and right atria contract, pushing all of the blood within their chambers down into the left and right ventricles. This process fills the ventricles to capacity and completes ventricular diastole. Cardiac diastole actually has two components: it contains the complete process of atrial filling, or atrial diastole, but only the first half of ventricular diastole. The second half of ventricular diastole requires the right and left atria to empty their contents into the ventricles.

The process of ventricular contraction or ventricular systole begins after ventricular diastole is completed. As the left and right ventricles begin to contract, increasing blood pressure within the ventricles forces the AV valves to close. Closing the AV valves prevents blood from returning to the upper chambers of the heart (the right and left atria). Tendinous fibers connecting leaflets of the AV valves to the interior ventricular walls helps prevent the AV valves from prolapsing under the tremendous force exerted on them during ventricular contraction. At this early stage of ventricular contraction, called isovolumetric contraction, all 4 valves of the heart are closed.

The ventricles continue to contract, increasing the pressure inside the lower chambers to the point that the semilunar valves (the pulmonic and aortic valves) are forced open. Opening the semilunar valves allows blood to leave the ventricles and enter the pulmonic artery and aorta. This second half of ventricular systole is called ventricular ejection and completes the cardiac cycle.

After the ventricles are fully contracted the heart relaxes and expands to fill with blood once again (cardiac diastole).

Electrocardiography

The contractions of the heart are initiated by electrical signals carried through thick bundles of nerves located within the heart's muscular walls. An electrocardiograph detects the electrical signals through leads placed on the chest of the person being monitored. Electrocardiography is not a direct visualization of the heart's activity, however, an electrocardiogram (EKG or ECG) can help physicians determine whether the heart is moving through the phases of the cardiac cycle in a normal, coordinated fashion.

Each peak or wave of an ECG represents a specific electrical signal initiating a contraction within the heart. The signaling pathway controlling the cardiac cycle begins at the sinoatrial (SA) node. The SA node is a nerve bundle located on the right atria near the chamber's junction with the superior vena cava. Once a signal is generated at the SA node, it travels through the walls of the right atrium to the Atrioventricular (AV) node, which is located in the lower part of the muscular wall separating the two atrial chambers. From the AV node, the signal travels through to the bundle of His. The bundle of His is a nerve track located just above the intraventricular septum, a thick muscular wall separating the left and right ventricles. The bundle of His then splits into left and right nerve bundle branches within the intraventricular septum. The nerve bundle branches continue down towards the apex of the heart, the bottom most point of the ventricles. At the apex of the heart the nerve bundle branches then split into many nerve tracks called Purkinje fibers, which travel along the outer muscular walls of the left and right ventricles.

The first wave of the ECG (the P wave) is generated when atrial depolarization occurs at the SA node. This depolarization initiates atrial systole, the contraction of the left and right atria. On an ECG signal, the P wave appears as a small, rounded bump.

After the P wave, the ECG signal flattens as it travels through the atrial walls to the AV node.

At the AV node, there is a small dip in the ECG line (the Q wave), as the nerve signal leaves the AV node and travels though the bundle of His.

A large, sharp positive spike in the ECG line is generated as the nerve impulse travels down the left and right nerve bundle branches. This large positive spike is called the R wave.

The S wave represents the signal traveling from the nerve bundle branches of the intraventricular septum into the Purkinje fibers, initiating ventricular systole. On an ECG line, the S wave is a small downward deflection that, like the Q wave, often appears as a portion of the R wave.

The QRS complex collectively represents the nerve impulse passing from the AV node, down the intraventricular septum, and through the outer walls of the ventricles, causing the outer walls of the ventricles to contract.

After the QRS complex, the ECG signal flattens before increasing in a rounded peak representing the repolarization of the ventricles as the ventricles relax post-systolic contraction, called the T wave.

Some variation in the shape of an ECG line is normal. However, certain ECG aberrations are highly correlated with specific pathologies in the functioning of the heart.

One example of such a specific pathology is a premature ventricular contraction (PVC). A PVC is an extra heartbeat that occurs from an ectopic focus on the ventricle wall. One type of PVC is an R on T PVC, which may be especially dangerous in an acute ischemic situation because the ventricles may be more vulnerable to ventricular tachycardia or fibrillation. With an R on T PVC, the PVC occurs during the vulnerable period of ventricular repolarization, coincident with the peak of the T wave.

Another example of a specific pathology is ventricular tachycardia (VT or V-tach). VT occurs when improper electrical activation causes the ventricles to contract too quickly, interfering with the efficient movement and oxygenation of blood as it moves through the heart. If VT continues for extended periods of time, the body may be insufficiently supplied with oxygen. VT may result in ventricular fibrillation and turn into sudden death. VT can be diagnosed from an ECG showing a rate of greater than 120 beats per minute and at least three wide QRS complexes in a row. V-tach is classified as non-sustained versus sustained based on whether it lasts less than or greater than 30 seconds.

Non-limiting examples of intervals that can be monitored within an ECG to identify certain pathologies include:

RR interval, the time elapsed between two successive R waves of the QRS signal on the electrocardiogram. The RR interval is a function of intrinsic properties of the sinus node as well as autonomic influences;

Corrected RR interval (RRc), which adjusts the RR interval (using one or more mathematical correction formulas) for heart rate extremes to improve detection of patients at increased risk of ventricular arrhythmia;

RT interval, the time elapsed from the R wave to the end of the T wave;

QT interval, the time from the start of the Q wave to the end of the T wave. The QT interval represents the time taken for ventricular depolarization and repolarization (effectively the period of ventricular systole from ventricular isovolumetric contraction to isovolumetric relaxation); and Corrected QT interval (QTc), which adjusts the QT interval (using one or more mathematical correction formulas) for heart rate extremes to improve detection of patients at increased risk of ventricular arrhythmia.

IV. Systems

One aspect of the present disclosure can include a system 10 (FIG. 1) that can perform advanced cardiac waveform analytics (ACWA). The system 10 can be used for performing electrocardiographic waveform analysis, data presentation, and actionable alert generation. The system 10 can generate actionable alerts for cardiac maladies, including, but not limited to, cardiac arrhythmias, heart failure, impending cardiopulmonary arrest, acute coronary syndrome, or critical metabolic abnormalities. In some instances, the system 10 can account for physiologic confounding variables when determining when to issue an actionable alert for a specific patient. Additionally, the present disclosure includes a communication tool by which the displayed actionable alert can be highlighted, edited, annotated, exchanged by medical professionals, shared/discussed with patients, and exported to an electronic medical record system according to clinical relevancy.

The system 10 (FIG. 1) can include a computing device 12, which can be in communication with a wearable device 14 and a display device 16. The wearable device 14 can be associated with a patient. The wearable device 14 can be coupled to one or more electrodes that can collect electrocardiographic data. For example, electrocardiographic data can be continuously recorded and collected from skin surface electrodes. The wearable device 14 can send the electrocardiographic data to the computing device 12. The computing device 12 can perform ACWA on the electrocardiographic data and send a visualization of one or more cardiac analytics (e.g., wavelets) to the display device 16. The computing device 12 can also send actionable alerts to the display device 16. The actionable alert itself can be an unalterable insertion into the patient's EMR at a given time-stamp, which can be transmitted to the display device 16. Medical professionals can receive mobile device communications on the display device 16 analogous to a text message or push notification with visual, audible, and/or vibratory alert. The display device 16 can be associated with one or more medical professionals and can allow actions to be performed on the actionable alerts, thereby creating modified actionable alerts. For example, the display device 16 can be associated with an input mechanism (e.g., a touch screen, a keyboard, a mouse, or the like). Medical professionals can send the modified actionable alert to other medical professionals (e.g., for doctors to give a second opinion, for emergency response professionals to take action on the patient, for a physician-in-training to exchange the actionable alert or modified actionable alert with an attending physician outside the hospital, for a non-cardiac physician to send the actionable alert to a cardiologist for review and to receive a modified actionable alert, etc.). The computing device 12 can send the actionable alerts and/or modifications to the actionable alerts to an EMR associated with the patient with respective time stamps. The modified actionable alerts can be tracked much in the same manner as shared-space document editing; one may easily revert to the original actionable alert or to previous versions of modified actionable alerts. Additionally, the computing device 12 can also transmit other elements to the EMR, such as those which led to the generation of the actionable alert.

Figure 2:
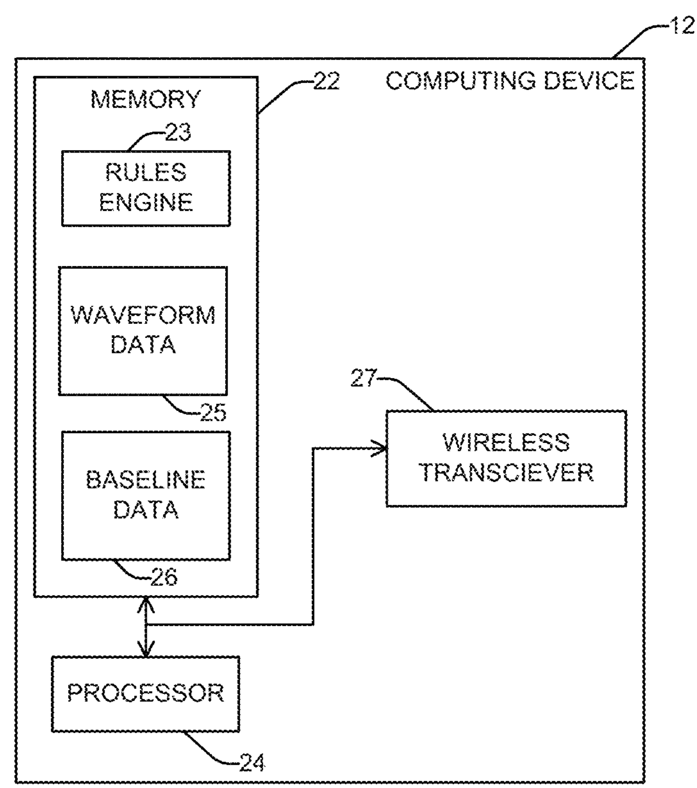
FIG. 2 is a block diagram showing an example of a computing device that can be used in the system of FIG. 1 to perform waveform analysis, data presentation, and actionable alert generation.

The computing device 12 is shown in more detail in FIG. 2. However, FIG. 2 does not show the complete detail of the computing device 12. The computing device 12 can include a non-transitory memory 22 configured to store instructions to implement a rules engine 23 and data. The computing device 12 can also include a processor 24 that can access the non-transitory memory 22 and execute the instructions to implement the rules engine 23. The non-transitory memory 22 can also store data, including electrocardiographic waveform data 25 (which can include cardiac analytics) and baseline data 26. The computing device 12 can include a wireless transmitter 27, which can allow communication with the wearable device 14, the display device 16, and the EMR (not shown). The wireless transmitter can communicate according to one or more protocols, including Bluetooth, cellular, WiFi, or the like. In some instances, the computing device 12 can also include a wired connection for data transmission.

Figure 3:
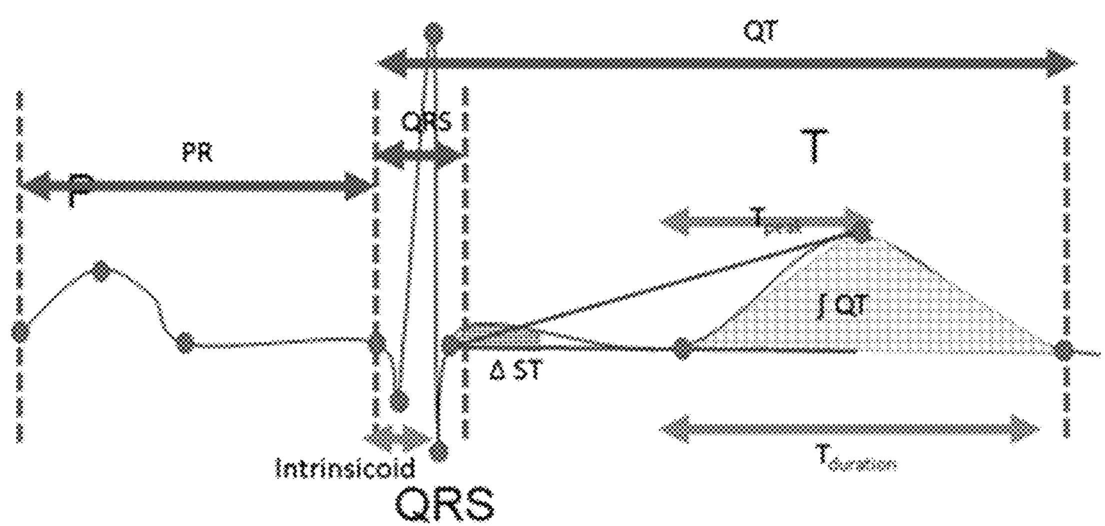
FIG. 3 is an example of a portion of an electrocardiographic waveform (ECG or EKG) for a cardiac cycle showing different cycle measurements and derivations that may be needed to perform ACWA.

In operation, the computing device 12 can receive electrocardiographic waveform data from the wearable device 14 associated with the patient. The computing device 12 can perform a mathematical analysis of the electrocardiographic waveform data 25 to provide cardiac analytics. For example, the cardiac analytics can be wavelets taken from the electrocardiographic waveform data 25 (either from a single cardiac cycle or a plurality of cardiac cycles). Examples of different parts of the electrocardiographic waveform data 25 are shown in FIG. 3. The cardiac analytics can include, but are not limited to, a PR interval, an RR interval, a RRc interval, an RT interval, a QRS duration time interval, an intrinsicoid time interval, a QT time interval, a QTc interval, a modified moving average of the QT interval, a T-peak amplitude voltage (as a highest absolute value of T maximum to T minimum voltage), a T-peak-to-terminus time interval, an ST angle as a linear regression of a ST segment, a measurement of ST amplitude change from baseline, QRS and QT waveform tracings, a percentage of X,Y coordinates aligning with a patient-specific template for the QRS waveform morphology, a percentage of X,Y coordinates aligning with a patient-specific template for the QT waveform morphology, and an area under the curve of the X,Y plot for the QT-waveform morphology. In each case, the cardiac analytics are determined automatically according to ACWA procedures. A visualization of the cardiac analytics can be generated and sent to the display device.

The rules engine 23 of the computing device 12 can perform a comparison between the cardiac analytics and the stored baseline data 26. The stored baseline data 26 can be specific to the patient (e.g., generated based on initially submitted data from the patient) and can ameliorate the effects of physiologic confounding variables. Enhanced sensitivity is achieved by each patient serving as his or her own control, in which percentage deviations from established norms and combination of the weighted metrics, using the patient-specific template and allowed normal ranges derived by the continuously collected clock-based data (e.g., showing temporal variation), are incorporated. Thus, both the individual waveform wavelet and the running trend for the important measurements can be analyzed continuously. In addition, the parameters for generating an actionable alert can be indication specific.

In some instances, the baseline data 26 to be used by the rules engine 23 can include population data for either patients similar to the patient (e.g., age, sex, severity of illness, weight, etc.) or for the population in general. This may be especially relevant in cases in which the patient is known or suspected to have an abnormal electrocardiograph due to a pathological disease state at the initiation of cardiac monitoring. In this scenario, the computing device 12 can select a 'normal' waveform template derived from population data matched according to the easily identified variables known to influence the normal cardiac waveform, including age, sex, race, and body mass index, entered at the time of monitoring initiation. If a non-patient specific 'normal' waveform is a poor match and generates excessive alarms at baseline, then the computing device 12 can allow suspension of the wavelet-based analytics until re-activated. A 'snooze' feature can be programmed to re-activate after a specified period of time unless programmed otherwise. The non-wavelet basic and advanced analytics can continue to operate while wavelet match is suspended.

The rules engine 23 can perform a series of logical comparisons (e.g., one or more wavelet comparisons) between the cardiac analytics and the baseline values, and provide a value based on the comparison. The value can indicate a clinically relevant state, such as the presence or absence of a general or specific cardiac pathology. A decision can be made by the rules engine 23 whether or not to generate an actionable alert for the electrocardiographic waveform data based on the value (e.g., whether the value exceeds one or more thresholds set for providing the actionable alert). When the actionable alert is generated, it is sent to the display device 16 in connection with a tactile, audio, or visual alarm. At least one of the electrocardiographic data, the cardiac analytics, the value, and/or the actionable alert can be transmitted to an EMR associated with the patient (each associated with a time stamp).

The rules engine 23 can determine when actionable alerts are to be generated. As an example, the rules engine 23 can perform both categorical and continuous variable analysis of one or more cardiac analytics (e.g., QT and RT interval data that is continuously collected) and report results of the analysis on a dashboard user interface radial display in a 24-hour time domain. Within this context, significant deviation from baseline values and/or violation of specific absolute values can trigger a series of rules engine and logic comparisons by which one or more of the cardiac analytics are measured. A number of heart beats collected within a beat buffer sample (e.g., a listening window) are measured and analyzed for the concomitant presence of ventricular ectopic heart beats and/or VT. The precise coupling intervals on the R-T time measurement are compared with the R-R interval for the abnormal beats when determining whether an actionable alert should be generated regarding the presence of pathologic QT prolongation with a high probability for serious life-threatening ventricular cardiac arrhythmias. The rules engine 23 may also incorporate other clinical variables of interest and/or physiologic confounding variables. The rules engine can utilize individual patients as their own control, and the morphologic features are compared with the stored template in real-time.

The present disclosure may provide complete (or semi-complete) automation of the continuous cardiac rhythm monitoring process, removing the need for human electrocardiographic assessment and review of ACWA-generated actionable alerts prior to their insertion into the patient's medical record. Advanced pattern-recognition programs and/or machine learning algorithms, as implemented by the ACWA, may allow for a fully automated cardiac monitoring system, limiting the potential for human error and enhancing the ability to identify subtle, high-risk cardiac rhythm patterns. Short of complete automation, the system 10 can mitigate the eventuality of introduced human error.

Example Use of the Rules Engine 23 to Detect Cardiac Abnormalities

In some instances, the rules engine 23 can: (1) receive electrocardiographic waveform data from a wearable device 14 associated with the patient; (2) perform a mathematical analysis of at least a portion of the electrocardiographic waveform data to provide cardiac analytics (e.g., an RR interval, an RT interval, a QT interval, a RRc interval, a QTc interval, or the like); (3) detect certain flags within a portion of the electrocardiographic waveform data and/or the cardiac analytics which may be signs related to a cardiac abnormality (e.g., the flag can be a pathologically prolonged QT interval, which can co-occur with an R on T PVC, and/or a VT from one or more of the cardiac analytics; and (4) generate an actionable alert when the cardiac abnormality is detected (e.g., the R on T PVC and/or the V-Tac). The actionable alert can be displayed with a visualization of one or more of the cardiac analytics.

In the example where the pathologically prolonged QT interval flag is detected, the rules engine 23 can be triggered to perform further analysis for a certain time period to see if the R on T PVC and/or the VT are detected. If the further analysis reveals no (or only one) pathologically prolonged QT interval, R on T PVC, or VT during the certain time period, then the system 10 continues to monitor the electrocardiographic waveform data without generating an actionable alert. However, the rules engine 23 generates an actionable alert when one of the following combinations is detected within the certain time period: a pathologically prolonged QT interval and an R on T PVC, a pathologically prolonged QT interval and a VT, or a pathologically prolonged QT interval and both an R on T PVC and a VT.

The certain time period can be a predefined listening window (the rules engine 23 may be programmed with one or more listening windows triggered by different situations). For example, the listening window can be identified within the electrocardiographic waveform data by determining whether the QTc is abnormal for a majority of sequential heartbeats (e.g., 2 heartbeats, 3 heartbeats, 4 heartbeats, etc.). The number of sequential heart beats can be 80 heart beats, 40 heart beats, or any given number of sequential heartbeats. An abnormal corrected QT interval can be patient specific, when the QTc interval is compared with a patient's previously acquired baseline QTc interval.

When the rules engine 23 detects an abnormal QTc interval, the listening window is triggered. After the listening window is triggered, the computing device 12 monitors the ECG for additional high-risk features. If no additional high risk features are detected during the listening window (e.g., when QTc is normal for all or the majority (a value between 50%-100%, which may be predefined for the particular patient) of sequential heartbeats) no actionable alert is issued. An actionable alert is generated when a VT or an R on T PVC is detected.

After the listening window is trigged, the computing device 12 and/or the rules engine 23 can determine and/or utilize additional patient information to aid with the ACWA analysis. For example, the additional patient information can include an indication of whether a bedside monitor associated with the patient is sending an alarm for the patient. This can be used as an additional check for the ACWA analysis. For example, the alarm sent by the monitor can be a PVC alarm for an R on T PVC. When the monitor is sending a PVC alarm, the computing device can localize the R on T PVC within the electrocardiographic waveform data by isolating the RR interval of the R on T PVC on the electrocardiographic. The computing device then computes an average RT over at least two heart beats and compares the RR interval with the average RT. When the isolated RR interval is less than or equal to the average RT, the rules engine 23 generates an actionable alert. As another example, the alarm can be a VT alarm for a VT. If the monitor is sending a VT alarm, then the rules engine 23 generates an actionable alert. If the computing device detects no additional high-risk features and/or alarms and the QTc interval is normal for a majority of sequential heart beats in the listening window, then the rules engine generates no actionable alert and ends the listening window. However, the PVC and VT processes may occur without the generation of an alarm by a bedside monitor and, instead, the PVC or VT may be identified and an actionable alert sent by detection of one or more abnormal cardiac analytics during a time period.

Mathematical Example

This Example shows how the R on T PVC and/or VT can be identified within electrocardiographic waveform data.

A pathologically prolonged QT interval is detected by using a listening window to observe the QTc interval in the determined cardiac analytics. For example, the listening window can be 40 heartbeats in length. If the QTc interval is consistently greater than 550 ms for the majority of the listening window, for example 30 out of 40 heartbeats, then the computing device must determine if an R on T PVC and/or a VT are co-occurring in the patient. If no pathologically prolonged QT interval is detected, then the listening window ends and no actionable alert is generated.

An R on T PVC can be detected by the computing device 12 if a PVC alarm associated with the patient is alarming. Additionally, an R on T PVC can be detected when the rules engine 23 analyzes the electrocardiographic waveform data and locates a PVC complex, an RR interval minimum within a select number of heartbeats (for example, 10 heartbeats) of the listening window, and then the computing device 12 computes the average RT interval over the listening window plus the select number of heartbeats, and compares the RR interval minimum of the PVC complex with the computed average RT interval. If the RR interval minimum of the PVC complex is less than or equal to the average RT interval then the computing device 12 detects an R on T PVC. When the computing device 12 detects at least both a pathologically prolonged QT interval and an Ron T PVC, then the computing device 12 generates an actionable alert.

A VT can be detected by the computing device 12 if a VT alarm associated with the patient is alarming or if the rules engine 23 detects the presence of a VT in the analyzed electrocardiographic waveform data. When the computing device 12 detects at least both a pathologically prolonged QT interval and a VT, then the computing device 12 generates an actionable alert.

V. Methods

Another aspect of the present disclosure can include methods shown in FIGS. 4, 5, 6, 7, and 8 for performing advanced cardiac waveform analytics (ACWA). The methods are illustrated as a process flow diagram with flowchart illustrations. For purposes of simplicity, the methods are shown and described as being executed serially; however, it is to be understood and appreciated that the present disclosure is not limited by the illustrated order, as some steps could occur in different orders and/or concurrently with other steps shown and described herein. Moreover, not all illustrated aspects may be required to implement the methods.

The methods can be executed by hardware—for example, the methods can be performed primarily by the computing device 12 of the system 10 of FIG. 1. One or more hardware elements of the computing device 12 of system 10 can execute software routines to implement at least a portion of each of the methods. Additionally, one or more elements of the computing device 12 of system 10 can include a non-transitory memory 22 storing the software routines and one or more processors 24 to execute the software routines corresponding to at least the portion of the methods. Other components (wearable device 14, display device 16, etc.) of the system 10 of FIG. 1 may also be used to facilitate the methods.

Figure 4:
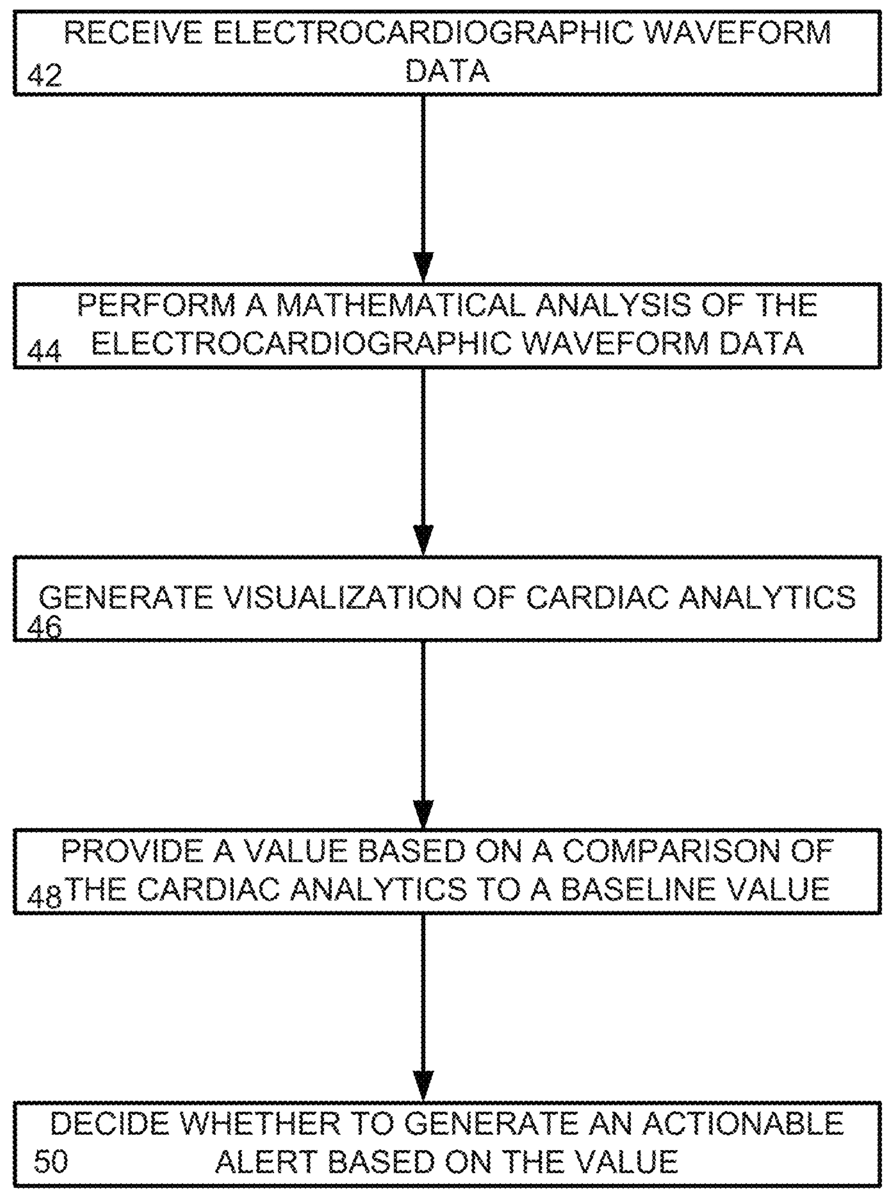
FIG. 4 is a process flow diagram illustrating a method for performing ACWA in accordance with another aspect of the present disclosure.

Referring now to FIG. 4, illustrated is a method for performing ACWA. At 42, electrocardiographic waveform data can be received. The electrocardiographic waveform data can be recorded by one or more skin surface electrodes and transmitted by a wearable device (e.g. wearable device 14) associated with a patient. At 44, a mathematical analysis can be performed on the electrocardiographic waveform data. For example, specific features of the electrocardiographic waveform can be isolated and pulled from the entire electrocardiographic waveform (one or more cardiac cycles). Based on the mathematical analysis, one or more cardiac analytics can be provided.

At 46, a visualization of cardiac analytics can be generated. The visualization can be generated, for example, on a dashboard display. The visualization can be sent to a display device (e.g., display device 16) to be displayed to (and/or used by) a medical professional. The cardiac analytics can also be associated with the patient and sent to an EMR of the patient with a time stamp.

At 48, a value can be provided based on a comparison of the cardiac analytics to a baseline value. For example, the comparison can be based on a correlation between the electrocardiographic waveform and at least one baseline value, wavelet-matching between the electrocardiographic waveform and the baseline waveform, and/or a specific alteration of any of the cardiac cycle measurement associated with a clinically relevant event. The baseline value can be a patient-specific baseline value. However, in other instances, the baseline value can be for patients similarly situated (e.g., same sex, same weight, same age, etc.). In other instances, the baseline value can be one for the population in general. The computing device can use a rules engine (e.g. rules engine 23) to apply a series of logical comparisons between the electrocardiographic waveform data and the baseline value, which can be stored in or accessed by the rules engine 23. Based on the comparisons by the rules engine 23, the value can be generated. The value can account for physiologic confounding variables due to the specially selected baseline value. The rules engine 23 can determine whether the value indicates a disease state or a non-disease state. In some instances, the value can be sent to the EMR associated with the patient, and/or the value can be sent to a dashboard display or, in other instances, another graphical user interface for display as a tile or icon to denote a clinically relevant event.

At 50, a decision can be made as to whether an actionable alert will be generated based on the value. The decision can be based on whether the value satisfies a threshold (e.g., the disease state and/or a change in the disease state). The decision, in some instances, can be sent to the EMR associated with the patient. The actionable alerts can be for one or more cardiac maladies, including (but not limited to) cardiac arrhythmias, heart failure, impending cardiopulmonary arrest, acute coronary syndrome, or critical metabolic abnormalities. When the actionable alert is generated, the actionable alert can be sent to one or more medical professionals (e.g., via a messaging program) and displayed with the visualization of the cardiac analytics (e.g., on the display device 16). The actionable alert can be accompanied by a tactile, audio, or visual alarm. The actionable alert can be highlighted, edited, annotated, and exchanged by medical professionals and sent back to the computing device 12.

A modified actionable alert and/or the annotation to the actionable alert can be received and/or generated (e.g., by computing device 12). The computing device 12 can send the modified actionable alert to an EMR system and link the modified actionable alert to the original actionable alert. In the EMR, different actionable alerts can be displayed in order of relevance. The modified actionable alert can be sent by the computing device 12 to other medical professionals. For example, the medical professionals can send the modified actionable alert to other medical professionals (e.g., for doctors to give a second opinion, for emergency response professionals to take action on the patient, for a physician-in-training to exchange the actionable alert or modified actionable alert with an attending physician outside the hospital, for a non-cardiac physician to send the actionable alert to a cardiologist for review and to receive an modified actionable alert, etc.).

FIGS. 5-8 illustrate example uses of ACWA to detect certain cardiac anomalies. The examples shown in FIGS. 5-8 can be used in connection with the detection of R-on-T PVCs and/or VTs. In this use of ACWA, a pathologically prolonged QT interval is detected by using a listening window to observe the QTc interval in the determined cardiac analytics. For example, the listening window can be 40 heartbeats in length. If the QTc interval is consistently greater than 550 ms for the majority of the listening window, for example 30 out of 40 heartbeats, then it must be determined if an R on T PVC and/or a VT are co-occurring in the patient. If no pathologically prolonged QT interval is detected, then the listening window ends, and no actionable alert is generated.

An R on T PVC can be detected if a PVC alarm associated with the patient is alarming. Additionally, an R on T PVC can be detected when the electrocardiographic waveform data is analyzed and a PVC complex, an RR interval minimum within a select number of heartbeats, for example 10 heartbeats, is located in the listening window, and then the average RT interval over the listening window plus the select number of heartbeats is computed, and the RR interval minimum of the PVC complex is compared with the computed average RT interval. If the RR interval minimum of the PVC complex is less than or equal to the average RT interval then an R on T PVC is detected. When at least both a pathologically prolonged QT interval and an R on T PVC are detected concurrently, then an actionable alert is generated.

A VT can be detected if a VT alarm associated with the patient is alarming or if the presence of a VT is detected in the analyzed electrocardiographic waveform data. When at least both a pathologically prolonged QT interval and a VT are detected concurrently, then an actionable alert is generated.

Figure 5:
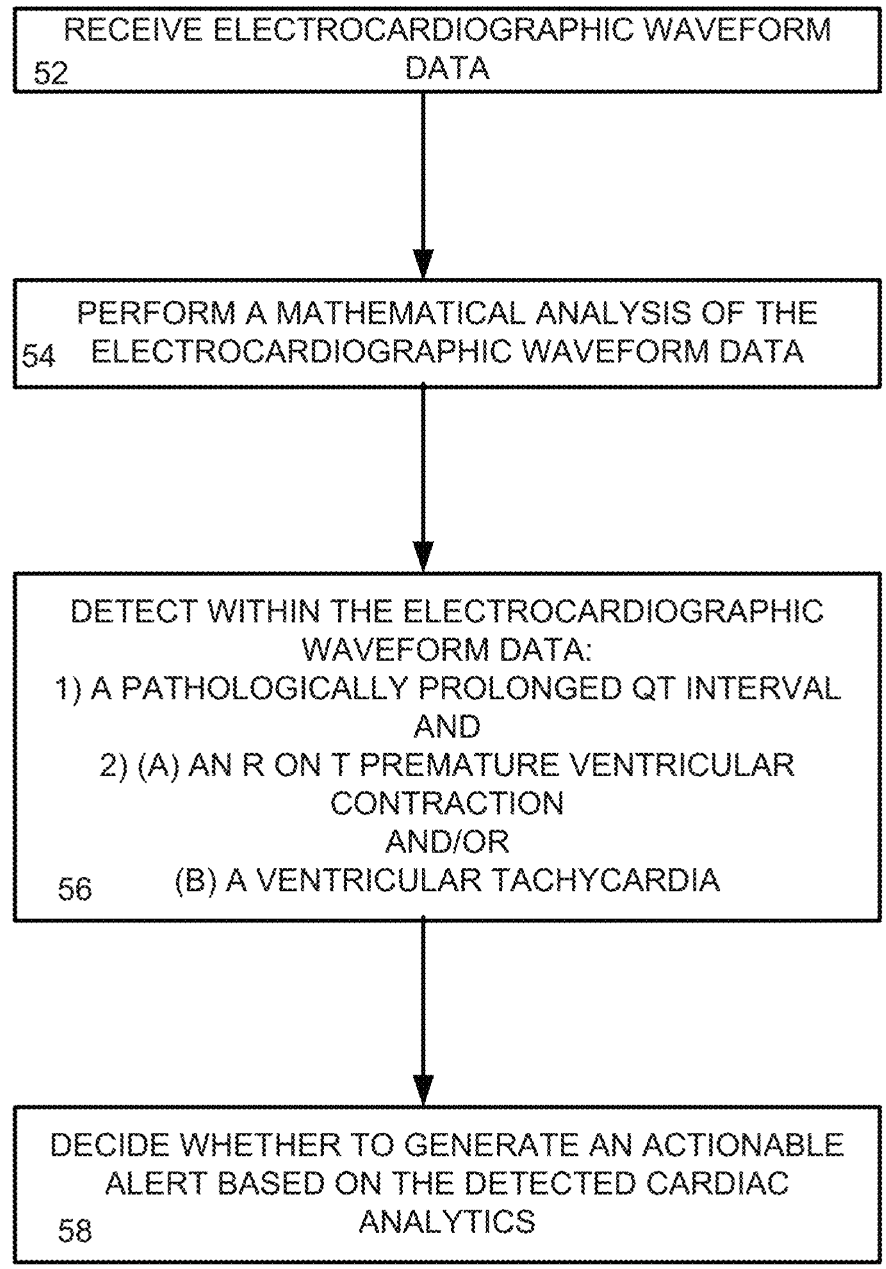
FIGS. 5-8 are process flow diagrams illustrating example methods for performing ACWA to detect certain cardiac anomalies.

Accordingly, referring now to FIG. 5, at 52, electrocardiographic waveform data can be received. The electrocardiographic waveform data can be recorded by one or more surface electrodes and transmitted by a wearable device (e.g., wearable device 14) associated with a patient. At 54, a mathematical analysis can be performed on the electrocardiographic waveform data. For example, specific features of the electrocardiographic waveform can be isolated and pulled from the entire electrocardiographic waveform (one or more cardiac cycles).

At 56, cardiac analytics can be detected within electrocardiographic waveform data based on the mathematical analysis. In this example, the cardiac analytics can include a pathologically prolonged QT interval. In this example, when the pathologically prolonged QT interval is detected, it can be determined from the cardiac analytics whether the patient is experiencing an R on T PVC, and a VT. At 58, a decision is made whether to generate an actionable alert, the decision is based on what cardiac analytics were detected. An actionable alert is generated if a pathologically prolonged QT interval and an R on T PVC are detected concomitant. An actionable alert is also generated if a pathologically prolonged QT interval and a VT are detected concomitant.

Figure 6:
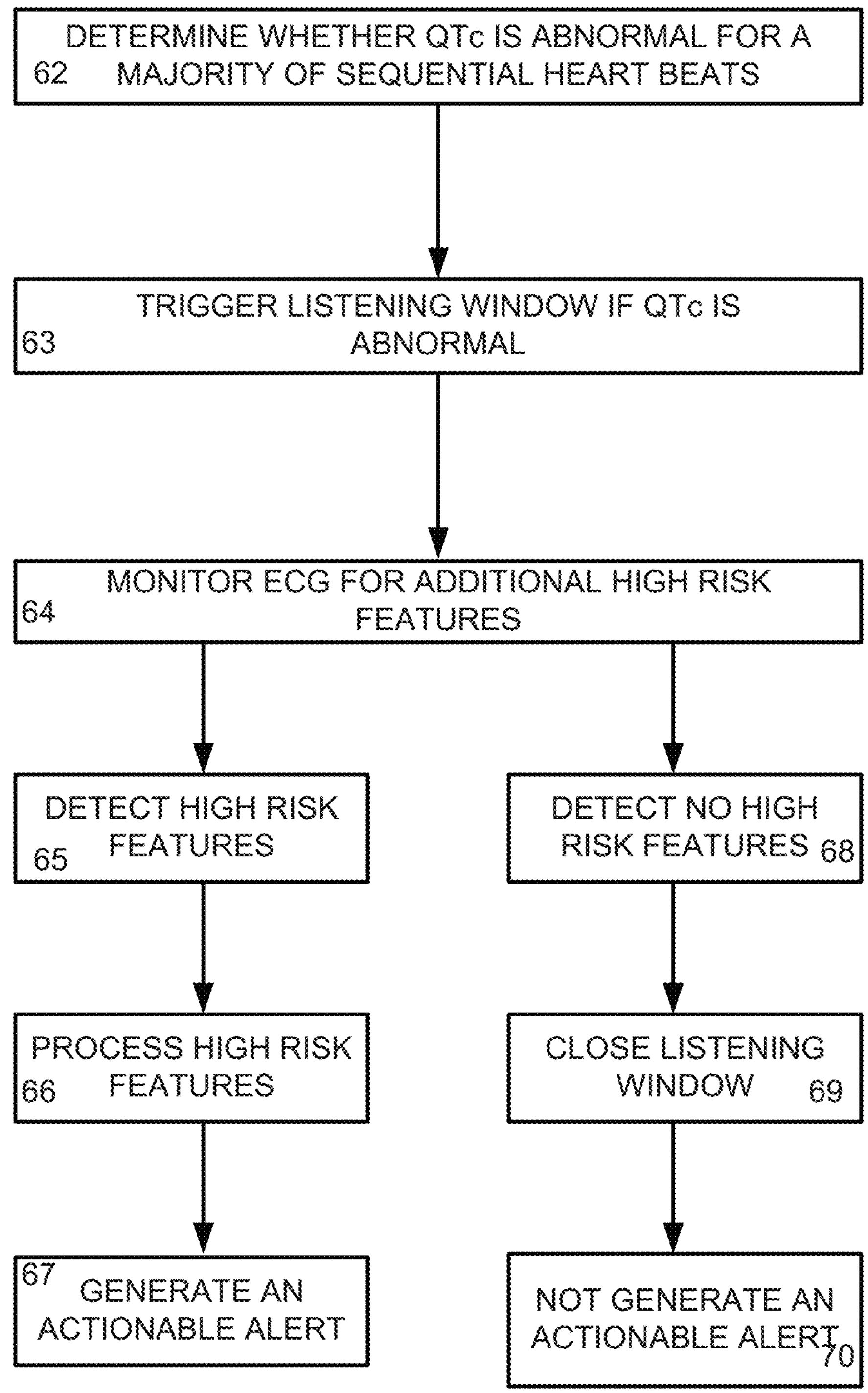

In FIG. 6, an example where the patient may be experiencing high risk features is illustrated. At 62, a QTc interval is determined to be normal or abnormal for a majority of sequential beats. At 63, if the QTc interval is determined to be abnormal, a listening window is triggered. At 64, when the listening window is triggered the ECG is monitored for additional high risk features. At 65, if high risk features are detected then, at 66, the high risk features are processed by cardiac analytics. At 67, if the high risk features meet a certain threshold an actionable alert is generated. At 68, if no high risk features are detected in the ECG then, at 69, the listening window closes and, at 70, no actionable alert is generated.

Figure 7:
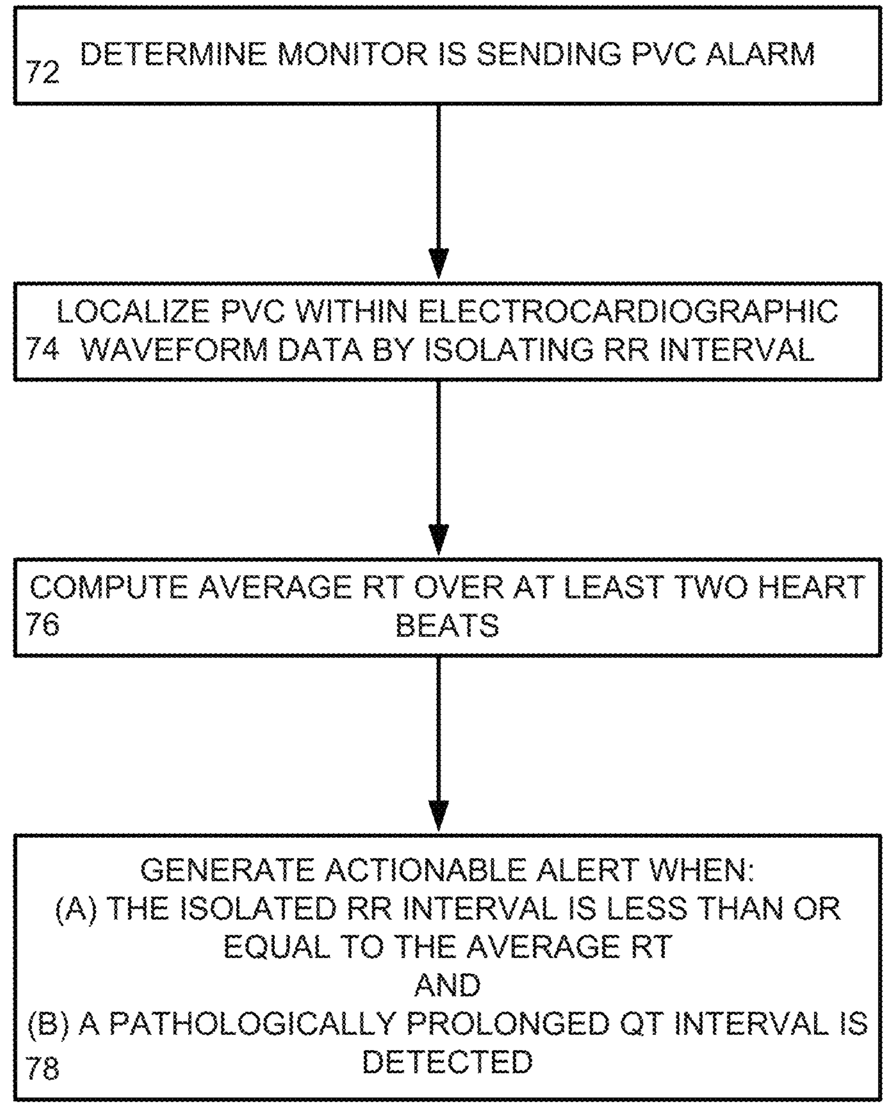
Figure 8:
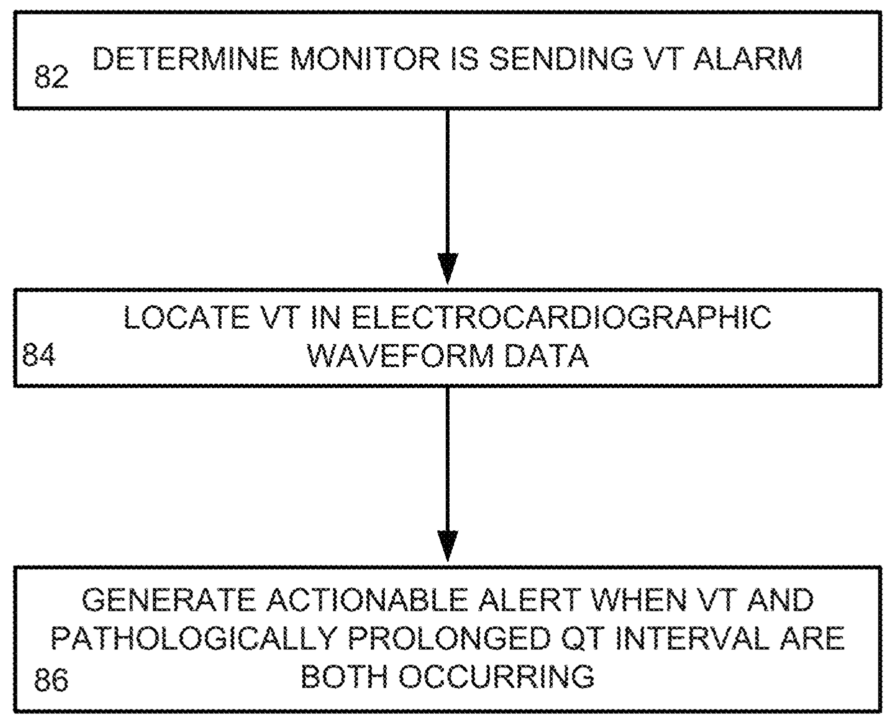

The processing of high risk features can include features indicating an R-on-T PVC (shown in FIG. 7) and/or a VT (shown in FIG. 8), for example. In FIG. 7, at 72, a bedside monitor is determined to be sending a PVC alarm. At 74, a PVC is localized within the electrocardiographic waveform data by isolating the RR interval surrounding the PVC. At 76, the average RT is computed over at least two heart beats of the electrocardiographic waveform data. At 78, an actionable alert is generated when the isolated RR interval is less than or equal to the average RT and a pathologically prolonged QT interval is detected within the listening window. Similarly, in FIG. 8, at 82, a bedside monitor is determined to be sending a VT alarm. At 84, the VT is located in the electrocardiographic waveform data. At 86, an actionable alert is generated when the VT is located within the same listening window as the pathologically prolonged QT interval.

From the above description, those skilled in the art will perceive improvements, changes and modifications. Such improvements, changes and modifications are within the skill of one in the art and are intended to be covered by the appended claims.

What is claimed is:

1. A method comprising:

receiving, by a system comprising a processor, electrocardiographic waveform data from a wearable device associated with a patient;

performing, by the system, a mathematical analysis of at least a portion of the electrocardiographic waveform data to provide cardiac analytics, wherein the cardiac analytics comprise wavelets from the electrocardiographic waveform data;

displaying, by a display device of the system, a visualization of one or more of the cardiac analytics;

detecting, by the system, from the cardiac analytics, within the at least the portion of the electrocardiographic waveform data:

a pathologically prolonged QT interval; and an R on T premature ventricular contraction and/or a ventricular tachycardia;

generating, by the system, differences between the pathologically prolonged QT interval and the R on T premature ventricular contraction and/or the ventricular tachycardia and at least one patient-specific baseline value to determine if the patient has a clinically relevant event;

generating, by the system, an actionable alert when the pathologically prolonged QT interval and the R on T premature ventricular contraction and/or the ventricular tachycardia are detected and the system has determined the patient has a clinically relevant event; and altering, by the system, the visualization of the one or more cardiac analytics on the display device when the actionable alert is generated.

2. The method of claim 1, wherein the pathologically prolonged QT interval and the R on T premature ventricular contraction and/or the ventricular tachycardia co-occur.

3. The method of claim 1, wherein the cardiac analytics comprise at least one of an RR interval, an RT interval, a QT interval, and a corrected QT interval (QTc).

4. The method of claim 3, further comprising identifying a listening window for the pathologically prolonged QT interval by determining whether the QTc is abnormal for a majority of sequential heart beats of the patient.

5. The method of claim 4, wherein when the listening window is identified, an ECG is monitored for additional high risk features, and wherein the listening window is closed when no additional high risk features have occurred, and the QTc is normal for a majority of sequential heart beats, no actionable alert is issued.

6. The method of claim 4, wherein when the listening window is identified, further comprising:

determining whether a monitor is sending a PVC alarm for premature ventricular contraction;

when the monitor is sending the PVC alarm:

localizing the PVC within the electrocardiographic waveform data by isolating the RR interval of the PVC;

computing an average RT over at least two heart beats; and when the isolated RR interval is less than or equal to the average RT, generating the actionable alert.

7. The method of claim 4, wherein when the listening window is identified, further comprising:

determining whether a monitor is sending a VT alarm for the ventricular tachycardia; and generating the actionable alert when the monitor is sending the VT alarm.

8. The method of claim 1, further comprising delivering, by the system, a notification to one or more medical professionals of the actionable alert.

9. The method of claim 1, wherein when the actionable alert is generated, the visualization is accompanied by a tactile alert, an audio alert, or a visual alert.

10. A system comprising:

a non-transitory memory storing instructions;

a processor to execute the instructions to:

receive electrocardiographic waveform data from a wearable device associated with a patient;

perform a mathematical analysis of at least a portion of the electrocardiographic waveform data to provide cardiac analytics, wherein the cardiac analytics comprise wavelets from the electrocardiographic waveform data;

generate a visualization of one or more of the cardiac analytics that are displayed on a display device;

detect from the cardiac analytics, within the at least the portion of the electrocardiographic waveform data:

pathologically prolonged QT interval; and an R on T premature ventricular contraction and/or a ventricular tachycardia;

generate differences between the pathologically prolonged QT interval and the R on T premature ventricular contraction and/or the ventricular tachycardia and at least one patient-specific baseline value to determine if the patient has a clinically relevant event;

generate an actionable alert when the pathologically prolonged QT interval and the R on T premature ventricular contraction and/or the ventricular tachycardia are detected and the system has determined the patient has a clinically relevant event; and alter the visualization of the one or more cardiac analytics on the display device when the actionable alert is generated; and a wireless transceiver to transmit the actionable alert and/or the visualization to one or more medical professionals; and the display device further configured to receive modifications to the actionable alert from the one or more medical professionals, wherein the modifications to the actionable alert are sent back to the processor, wherein the processor generates a modified actionable alert and visualization linked to the actionable alert.

11. The system of claim 10, wherein the pathologically prolonged QT interval and the R on T premature ventricular contraction and/or the ventricular tachycardia co-occur.

12. The system of claim 10, wherein the cardiac analytics comprise at least one of an RR interval, an RT interval, a QT interval, and a corrected QT interval (QTc).

13. The system of claim 12, wherein a listening window for the pathologically prolonged QT interval is identified by determining whether the QTc is abnormal for a majority of sequential heart beats.

14. The system of claim 13, wherein when the listening window is identified, an ECG is monitored for additional high risk features, and wherein the listening window is closed when no additional high risk features have occurred, and the QTc is normal for a majority of sequential heart beats, no actionable alert is issued.

15. The system of claim 13, when the listening window is identified, the processor further executes the instructions to:

determine whether a monitor is sending a PVC alarm for premature ventricular contraction;

when the monitor is sending the PVC alarm:

localize the PVC within the electrocardiographic waveform data by isolating the RR interval of the PVC;

compute an average RT over at least two heart beats; and when the isolated RR interval is less than or equal to the average RT, generate the actionable alert.

16. The system of claim 13, wherein when the listening window is identified, the processor further executes the instructions to:

determine whether a monitor is sending a VT alarm for the ventricular tachycardia; and generate the actionable alert when the monitor is sending the VT alarm.

17. The system of claim 10, wherein when the actionable alert is generated, the visualization is accompanied by a tactile alert, an audio alert, or a visual alert.

18. The system of claim 10, wherein the wireless transceiver is configured with at least one of cellular, Bluetooth, and WiFi transmission capabilities.

* * * * *